US00PP13859P39

(12) United States Plant Patent
Walters

(10) Patent No.: US PP13,859 P3
(45) Date of Patent: Jun. 3, 2003

(54) ***BRUNNERA MACROPHYLLA* PLANT NAMED 'JACK FROST'**

(76) Inventor: John D. Walters, 1992-96$^{th}$Ave., Zeeland, MI (US) 49469-0137

( * ) Notice: Subject to any disclaimer, the term of this patent is extended or adjusted under 35 U.S.C. 154(b) by 81 days.

(21) Appl. No.: 09/798,089

(22) Filed: Mar. 5, 2001

(65) Prior Publication Data

US 2002/0002719 P1 Jan. 3, 2002

(51) Int. Cl.$^{7}$ ..... A01H 5/00

(52) U.S. Cl. ..... Plt./263

(58) Field of Search ..... Plt./263

*Primary Examiner*—Howard J. Locker

(57) ABSTRACT

The new and distinctive cultivar of Brunnera named 'Jack Frost' characterized by an intense silver coating on top of the leaves with contrasting green veining and leaf edges, and light blue flowers in the spring, suitable for landscape or potted culture.

2 Drawing Sheets

SUMMARY, BACKGROUND AND ORIGIN OF THE PLANT

The new and distinct *Brunnera macrophylla* 'Jack Frost', hereinafter also referred to as 'Jack Frost' and "the plant," is a new and unique sport of the cultivar *Brunnera macrophylla* 'Langtrees' (not patented). I discovered the plant among some propagated *Brunnera macrophylla* 'Langtrees' plants in cultivation in the greenhouse of a nursery in Zeeland, Mich. It was a non-induced mutation. It has been asexually propagated, both by crown division, and by careful tissue culture propagation of shoot tips, at the same nursery in Zeeland, Mich. Both methods have produced plants identical to the originally discovered sport and maintain those unique characteristics in subsequent generations.

BRIEF DESCRIPTION OF THE DRAWINGS

The photographs of the new invention demonstrate the overall appearance of the plant including the unique traits. The colors are as accurate as reasonably possible with color reproductions. Light source direction may cause the appearance of variation in color.

DEATILED BOTANICAL DESCRIPTION OF THE PLANT

Figure 1:
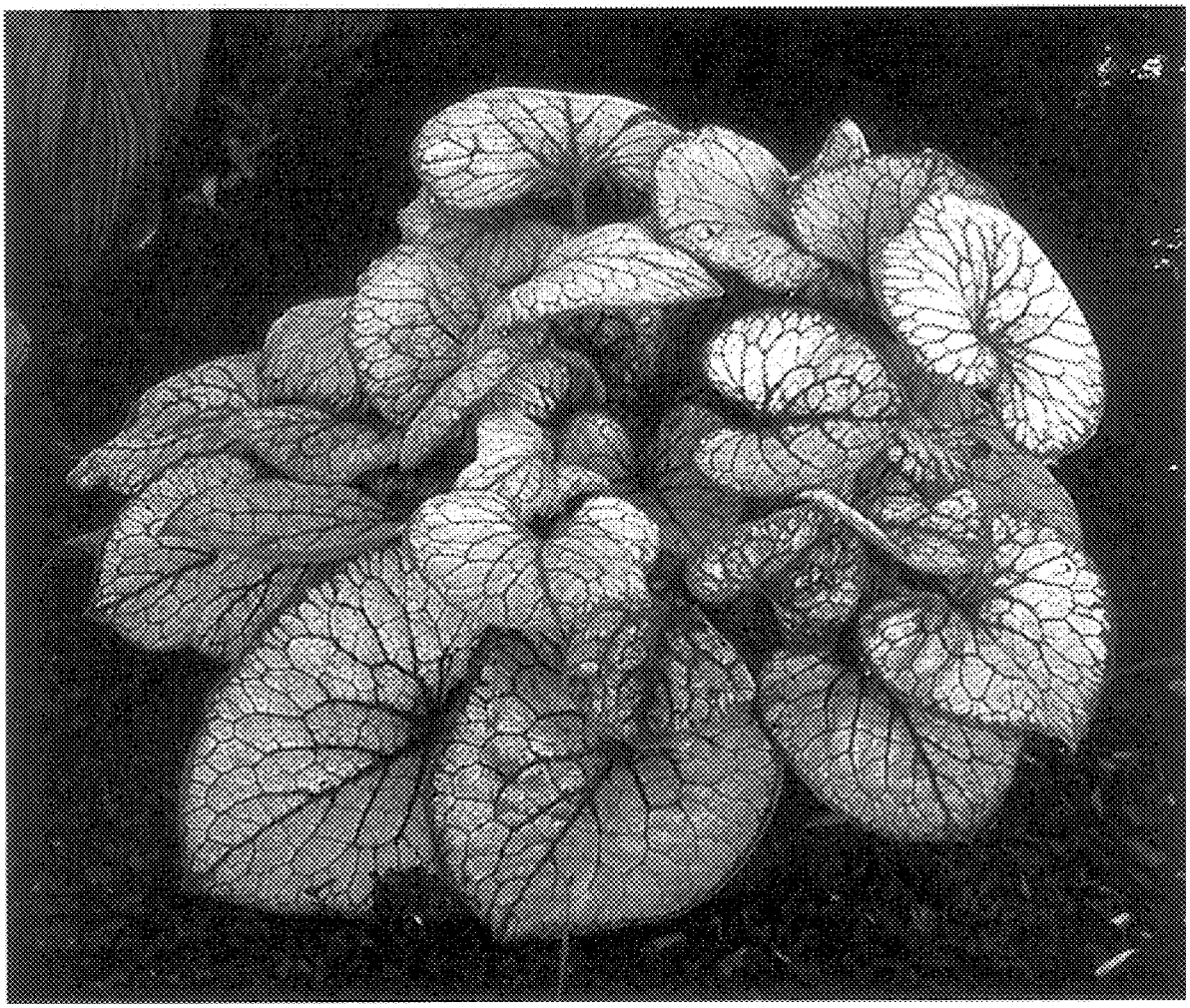
FIG. 1 shows the overall plant.
Figure 2:
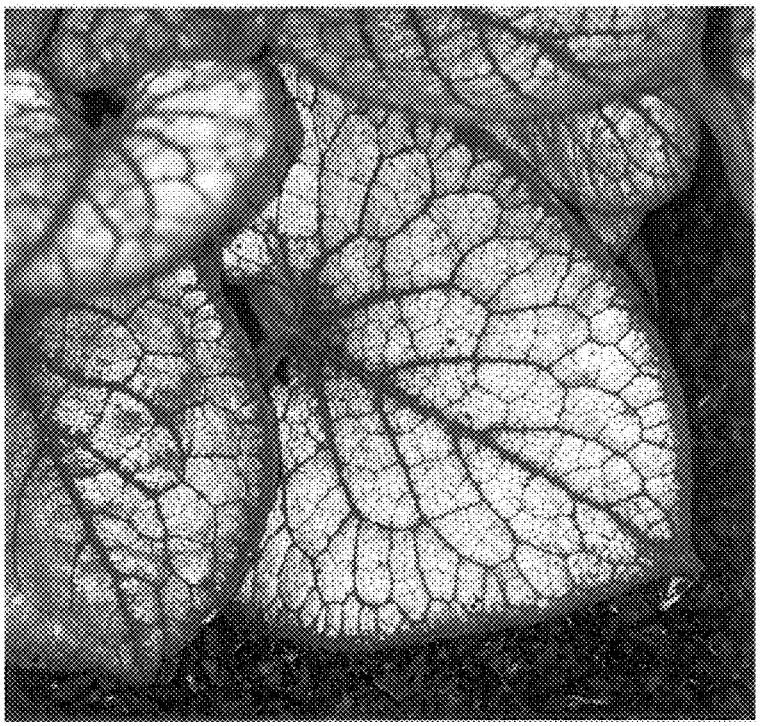
FIG. 2 shows a close-up of a few leaves with the unique variegation.
Figure 3:
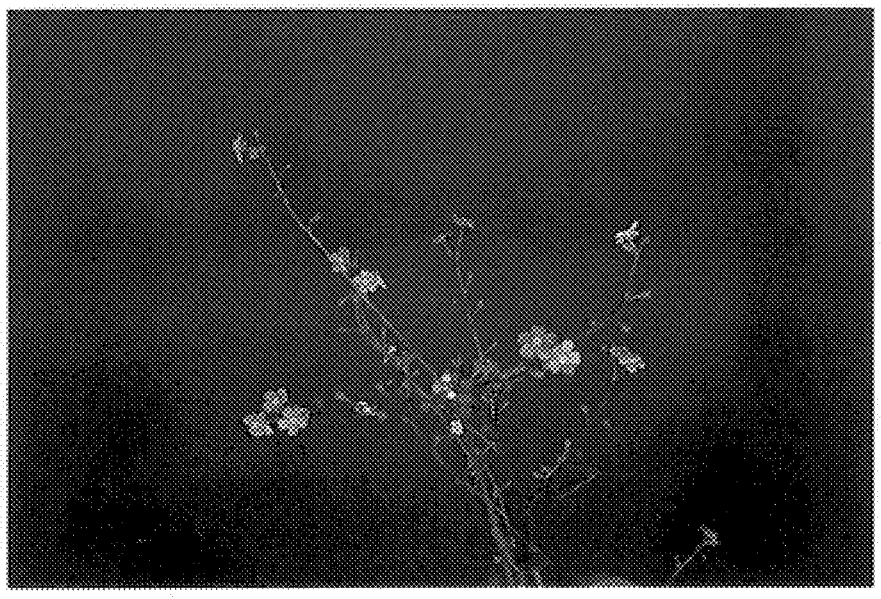
FIG. 3 shows the plant in flower.

*Brunnera macrophylla* (Adams) Johnst. is a hardy, herbaceous, subalpine perennial native to eastern Asia, western Caucasus and Mediterranean Europe. It has many common names, among them: Alkanet, Siberian Bugloss, and Forget-me-not.

*Brunnera macrophylla* 'Langtrees' (not patented) is an English cultivar with chevron-patterned silvery white spots on the leaves. Other selections of *Brunnera macrophylla* include: a white margined type named 'Variegata' (not patented), or also sometimes called 'Dawson's White' (not patented), white flowered forms called 'Betsy Baring' (not patented), 'Betty Bowring' (not patented) and Marley's White' (not patented), and a creamy yellow margined type named 'Hadspen Cream' (not patented) discovered by Eric Smith of England Brunnera 'Silver Wings' (U.S. Plant patent application Ser. No. 09/907,878) is another sport of 'Langtrees' with a very thin creamy white chimeral margin on the leaves. 'Silver Wings' has more green and much less of the silver on the upper leaf surface.

Brunnera 'Jack Frost' was discovered by me as a single, non-induced sport in a batch of tissue culture propagated plants of Brunnera 'Langtrees' in the spring of 1997 at a nursery in Zeeland, Mich. The single plant of 'Jack Frost' was grown to maturity and evaluated regularly at the same nursery. When large enough, the crown was divided into two pieces and further evaluated, and also propagated in test tubes using normal shoot tip tissue culture techniques at a nursery in Zeeland, Mich. Root initiation from shoots occurs in about one and one half to two and one half weeks. The unique characteristics held in both types of propagation methods, and expressed themselves completely in subsequent generations of plantlets. Crops finish off in 3" containers in about five months in greenhouse conditions and would be about 6 inches (15 cm) tall and 8 inches (20 cm) wide. The plant flowers the first spring following at least four months growth during the summer or fall.

The following descriptions with generic dictionary color usage are of a three-year-old plant growing in Zeeland, Mich. For more precise color descriptions The Royal Horticultural Colour Chart and the corresponding color references are used. The plant has not been evaluated in all possible growing environments. The phenotype may vary slightly with different conditions such as fertility, light, moisture and temperature, however the genotype remains stable.

The foliage reaches heights of 18 inches (45 cm) and forms compact clumps 24 to 36 inches (60 to 90 cm) wide. The leaves are cordate to reniform, coarsely pubescent, with long thin petioles basally attached to underground rhizomes.

Brunnera 'Jack Frost' is unique in one main characteristic. The foliage shape, type and structure are the same as the parent 'Langtrees', however the surface color of the foliage is coated with a silvery white frosting which covers almost the entire leaf except the primary and secondary veins and a rim around the outer ⅛ to ¼ inch (3 to 6 mm) of the leaves, giving the appearance of cracked porcelain. The silver white frosting is lighter than RHS 192 D or 190 D. The base leaf color is a rich green, about RHS 137 A or 137 B on the upper surface between the veins, and also about ⅛ to ¼ inch (3 to 6 cm) wide around the edge of the leaf. The leaf blades measure up to 6 inches (15 cm) long and wide. The pubescent petioles are ⅛ inch (3 mm) wide and up to 12 inches (30 cm) long. Petiole color is a RHS 142 B. Leaf underside is between RHS 143 A and 142 B. The leaf has no normal undulations but is flat to slightly convex, curling downward around the edges in some conditions.

The numerous flowers are held on paniculate cymes and have smaller ovate cauline leaves either sessile or with short petioles. Each inflorescence may have as many as 120 to 180 individual flowers on panicles up to 18 inches (45 cm) tall and branches to 6 inches (15 cm) wide, and remain in flower for three weeks. Each flower persists up to a week. The peduncles are pubescent, erect and a green RHS 138 B. Light blue rounded petals form a five-lobed corolla measuring up to ¼ inch (7 mm) diameter with a short white corolla throat. The adaxial side, or face of the corolla, is a sky blue between RHS 106 A and 107 B. The abaxial side, or back of the flower, is a much lighter blue, about 108 D. Flower buds are a RHS 76 C about four days prior to opening. The five sepals are about 1/16 inch (1 mm) and a green RHS 142 B. Flower timing is identical to *Brunnera macrophylla*, about late April to May, in Zeeland, Mich. The plant produces seed, and the seed and all the sexual organs are similar to the species: single gynoecium 3 mm long, about RHS 193 D: androecium, 5; stamens, white, about 2 to 3 mm long; anthers about 1 mm long and dark purple, RHS 187 A. Seeds are a small nutlet, less than 1 mm in diameter, dark brown to near black.

The plant is hardy to USDA zone 3. It has no serious pests. 'Jack Frost' performs well in shade, or sunny garden locations with some protection from the hottest sun. It grows best with an ample amount of moisture, but can tolerate drier gardens. It is also well suited for growing in containers, and is less prone to leaf scorch than 'Variegata'.

What is claimed is:

1. I claim a new and distinct perennial *Brunnera macrophylla* plant named 'Jack Frost', as herein described and illustrated.

* * * * *